United States Patent [19]

Bernstein et al.

[11] Patent Number: 5,435,303
[45] Date of Patent: Jul. 25, 1995

[54] MRA IMAGE PRODUCED BY TEMPORAL FLOW DATA SHARING

[75] Inventors: Matthew A. Bernstein; Thomas K. Foo, both of Waukesha, Wis.

[73] Assignee: General Electric Company, Milwaukee, Wis.

[21] Appl. No.: 263,573

[22] Filed: Jun. 23, 1994

Related U.S. Application Data

[63] Continuation-in-part of Ser. No. 102,166, Aug. 14, 1993, Pat. No. 5,377,680.

[51] Int. Cl.⁶ ............................................. A61B 5/055
[52] U.S. Cl. .................................. 128/653.3; 128/696; 128/708
[58] Field of Search ............... 128/653.1, 653.2, 653.3, 128/696, 708; 324/306, 309; 364/413.13, 413.18

[56] References Cited

U.S. PATENT DOCUMENTS

| | | | |
|---|---|---|---|
| 5,226,418 | 7/1993 | Bernstein et al. | 128/653.3 |
| 5,285,158 | 2/1994 | Mistretta et al. | 128/653.3 |
| 5,329,925 | 7/1994 | NessAiver | 128/653.3 |
| 5,348,011 | 9/1994 | NessAiver | 128/653.2 |
| 5,377,680 | 1/1995 | Bernstein et al. | 128/653.2 |

*Primary Examiner*—Krista M. Zele
*Attorney, Agent, or Firm*—Quarles & Brady

[57] ABSTRACT

Flow encoded NMR pulse sequences are employed to acquire data sets from which a set of angiographic images can be reconstructed depicting blood flow at successive phases during the cardiac cycle. The number of angiographic images is increased by selecting views from adjacent data sets to form interpolated data sets that are employed to reconstruct angiographic images depicting blood flow at cardiac phases between the successive phases.

9 Claims, 4 Drawing Sheets

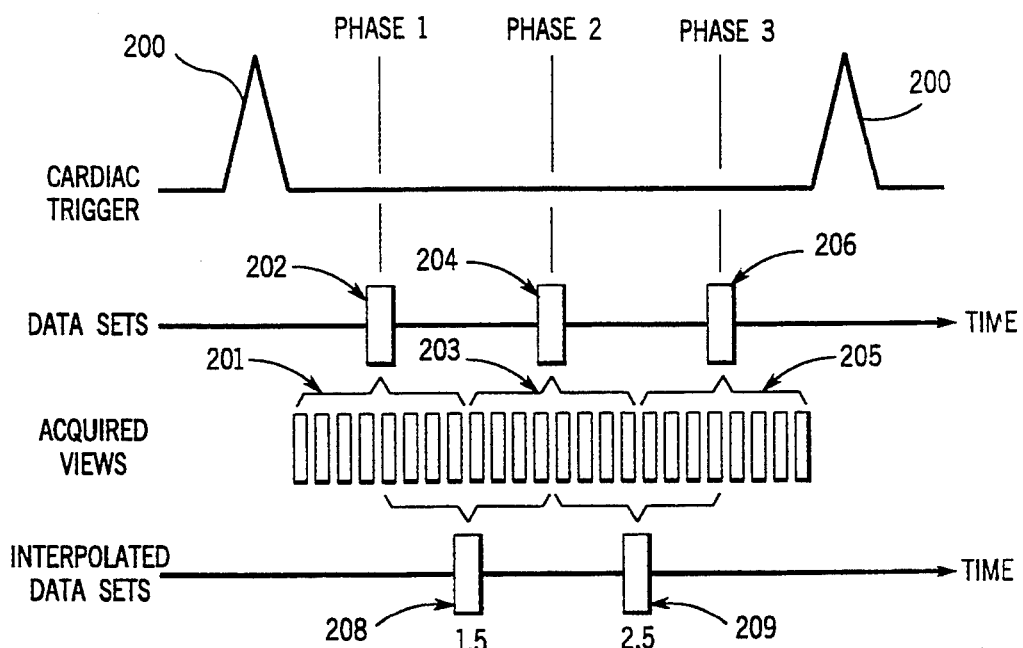
FIG. 2
FIG. 3
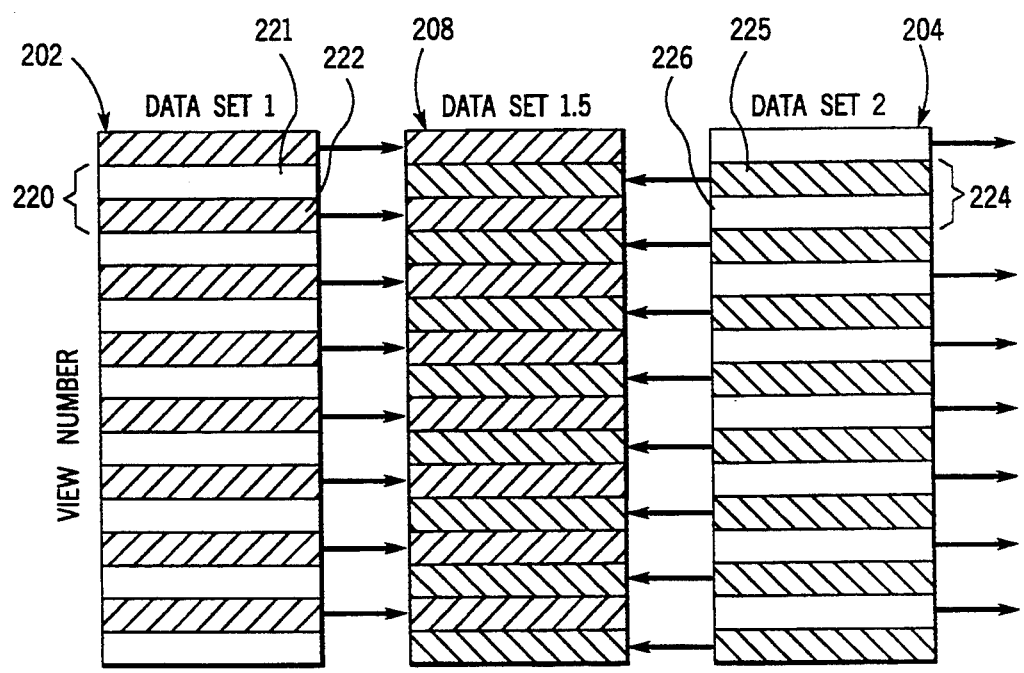

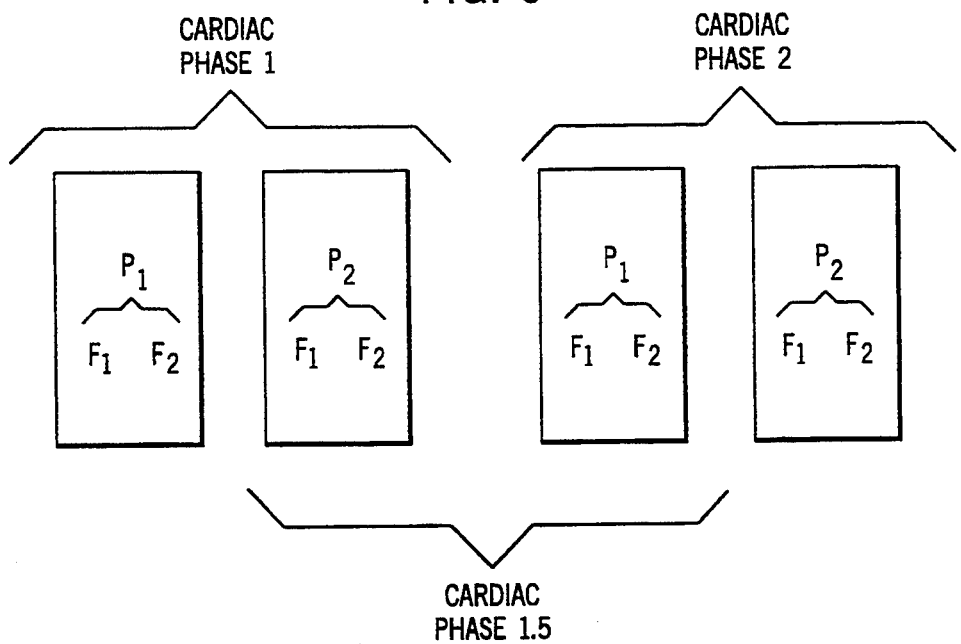
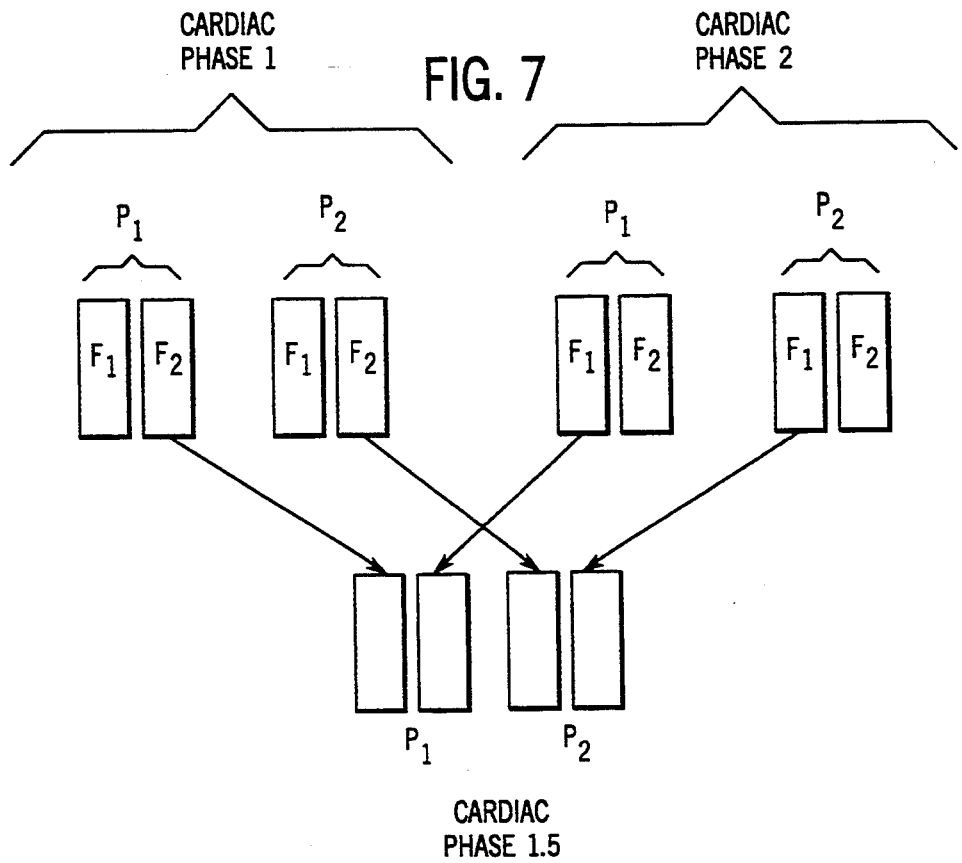

MRA IMAGE PRODUCED BY TEMPORAL FLOW DATA SHARING

RELATED PATENT APPLICATION

This application is a continuation-in-part of U.S. patent application Ser. No. 08/102,166, filed on Aug. 14, 1993 now U.S. Pat. No. 5,317,680, entitled "MRI Cardiac Image Produced By Temporal Data Sharing".

BACKGROUND OF THE INVENTION

The field of the invention is nuclear magnetic resonance imaging methods and systems. More particularly, the invention relates to phase contrast angiography.

When a substance such as human tissue is subjected to a uniform magnetic field (polarizing field $B_0$), the individual magnetic moments of the spins in the tissue attempt to align with this polarizing field, but precess about it in random order at their characteristic Larmor frequency. If the substance, or tissue, is subjected to a magnetic field (excitation field $B_1$) which is in the x-y plane and which is near the Larmor frequency, the net aligned moment, $M_z$, may be rotated, or "tipped", into the x-y plane to produce a net transverse magnetic moment $M_t$. A signal emitted by the excited spins may be received after the excitation signal $B_1$ is terminated and processed to form an image.

When utilizing these signals to produce images, magnetic field gradients ($G_x$ $G_y$ and $G_z$) are employed. Typically, the region to be imaged is scanned by a sequence of measurement cycles in which these gradients vary according to the particular localization method being used. The resulting set of received NMR signals are digitized and processed to reconstruct the image using one of many well known reconstruction techniques.

Most NMR scans currently used to produce medical images require many minutes to acquire the necessary data. The reduction of this scan time is an important consideration, since reduced scan time increases patient throughput, improves patient comfort, and improves image quality by reducing motion artifacts. There is a class of pulse sequences which have a very short repetition time (TR) and result in complete scans which can be conducted in seconds rather than minutes. When applied to cardiac imaging, for example, a complete scan from which a series of images showing the heart at different phases of its cycle can be acquired in a single breath-hold.

The number of cardiac phase images that can be acquired during a scan is determined by a number of factors such as pulse sequence repetition time, the number of views acquired at each cardiac trigger and the patient's heart rate. By decreasing the number of views acquired at each cardiac trigger, more phase images can be acquired and the "temporal resolution" of the series of cardiac images is increased. However, total scan time is increased as the number of views acquired per cardiac trigger is reduced and the number of cardiac triggers required to complete acquisition of an image with the same spatial resolution increases.

The same temporal resolution problem exists when flow encoded acquisitions are made to produce a magnetic resonance angiogram. In addition to the different phase encoded views required to reconstruct each image, at least two flow encoded views are required at each phase encoding in order to reconstruct an angiographic image. As used in this patent, the term "view" encompasses both phase encoding view and flow encoding view. If flow is to be measured along all three axes, a minimum of four flow encoding views are required at each phase encoding, and the task of providing high temporal resolution within a short scan time is even more difficult.

SUMMARY OF THE INVENTION

The present invention is a method for increasing the number of cardiac phase angiographic images that can be acquired during a scan with a given pulse sequence. More specifically, the present invention includes producing a cardiac signal which indicates the patient's cardiac cycle; acquiring a plurality of flow encoded NMR data sets from which angiographic images are reconstructed that depict blood flow at a corresponding succession of phases in the cardiac cycle; producing an intermediate flow encoded NMR data set by combining NMR data selected from two temporally adjacent NMR data sets; and reconstructing an angiographic image from the intermediate NMR data set which depicts blood flow at a cardiac phase between the phases depicted by the temporally adjacent NMR data sets.

An object of the invention is to improve the temporal resolution of a series of angiographic images without increasing the total scan time. Without acquiring any additional NMR data, the present invention enables one to increase the number of cardiac images that can be reconstructed. Specifically, if n data sets are acquired during the scan, n−1 intermediate NMR data sets can be formed and a total of 2n−1 images can be reconstructed. The intermediate images depict the blood flow at cardiac phases midway between the acquired phases to effectively double the temporal resolution. This is important to visualize states which persist for very short intervals, such as end-systole, which may be averaged out with rapid cardiac motion if the interval between images is too long.

BRIEF DESCRIPTION OF THE DRAWINGS

FIG. 2 is a graphic representation of the data acquisition sequence performed by the MRI System of FIG. 1;

FIG. 3 is a schematic representation of how an interpolated image data set is formed from data acquired with the data acquisition sequence of FIG. 2;

FIG. 6 is a graphic representation of another data acquisition sequence for phase contrast angiography; and FIG. 7 is a graphic representation of yet another data acquisition sequence for phase contrast angiography.

DESCRIPTION OF THE PREFERRED EMBODIMENT

Figure 1:
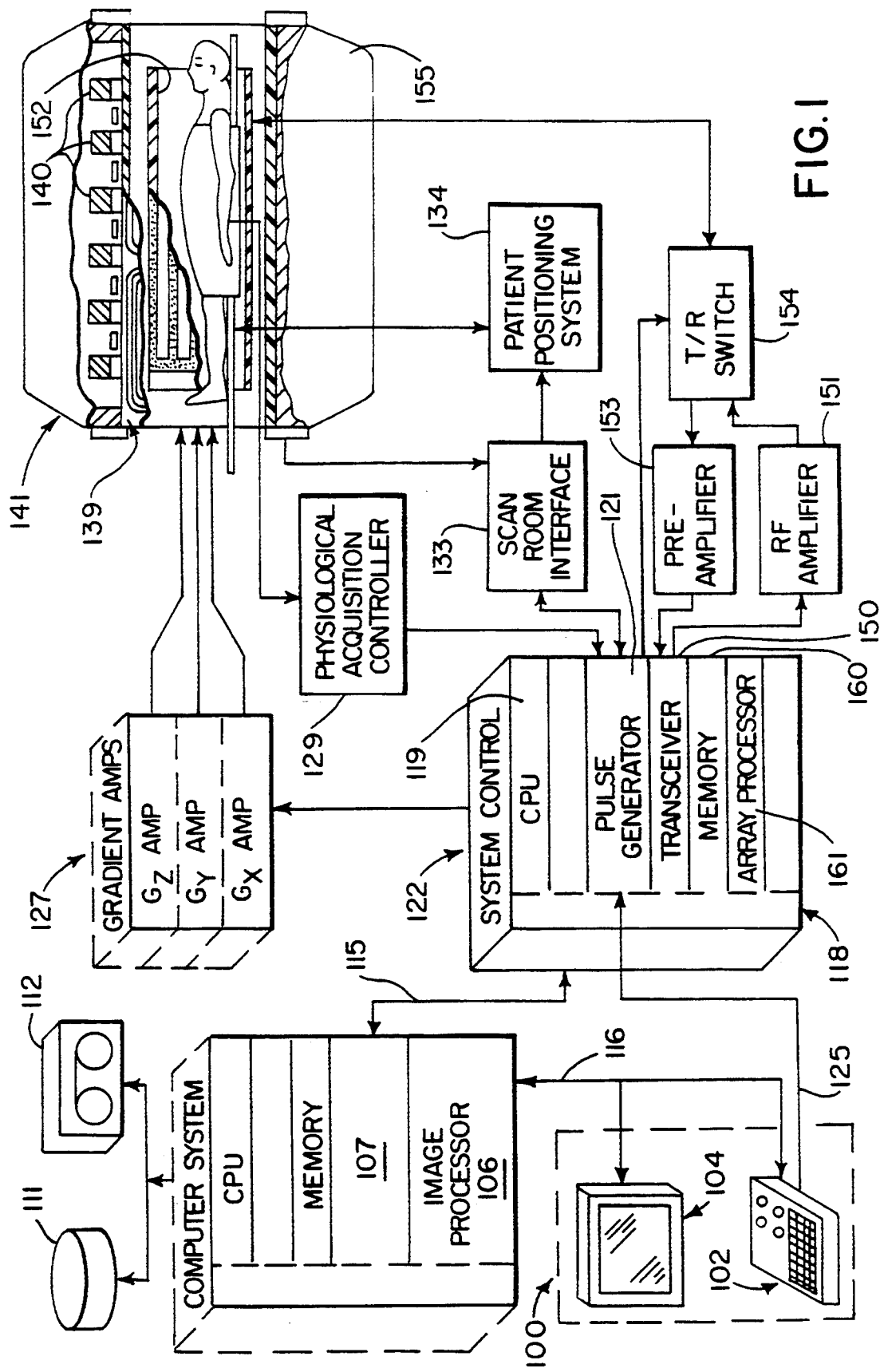
FIG. 1 is a block diagram of an MRI system which employs the present invention.

Referring first to FIG. 1, there is shown the major components of a preferred MRI system which incorporates the present invention. The operation of the system is controlled from an operator console 100 which includes a keyboard and control panel 102 and a display 104. The console 100 communicates through a link 116 with a separate computer system 107 that enables an operator to control the production and display of images on the screen 104. The computer system 107 includes a number of modules which communicate with each other through a backplane. These include an image processor module 106, a CPU module 108 and a memory module 113, known in the art as a frame buffer for storing image data arrays. The computer system 107 is linked to a disk storage 111 and a tape drive 112 for storage of image data and programs, and it communicates with a separate system control 122 through a high speed serial link 115.

The system control 122 includes a set of modules connected together by a backplane. These include a CPU module 119 and a pulse generator module 121 which connects to the operator console 100 through a serial link 125. It is through this link 125 that the system control 122 receives commands from the operator which indicate the scan sequence that is to be performed. The pulse generator module 121 operates the system components to carry out the desired scan sequence. It produces data which indicates the timing, strength and shape of the RF pulses which are to be produced, and the timing of length of the data acquisition window. The pulse generator module 121 connects to a set of gradient amplifiers 127, to indicate the timing and shape of the gradient pulses to be produced during the scan. The pulse generator module 121 also receives patient data from a physiological acquisition controller 129 that receives signals from a number of different sensors connected to the patient, such as ECG signals from electrodes or respiratory signals from a bellows. And finally, the pulse generator module 121 connects to a scan room interface circuit 133 which receives signals from various sensors associated with the condition of the patient and the magnet system. It is also through the scan room interface circuit 133 that a patient positioning system 134 receives commands to move the patient to the desired position for the scan.

The gradient waveforms produced by the pulse generator module 121 are applied to a gradient amplifier system 127 comprising $G_x$, $G_y$ and $G_z$ amplifiers. Each gradient amplifier excites a corresponding gradient coil in an assembly generally designated 139 to produce the magnetic field gradients used for position encoding acquired signals. The gradient coil assembly 139 forms part of a magnet assembly 141 which includes a polarizing magnet 140 and a whole-body RF coil 152. A transceiver module 150 in the system control 122 produces pulses which are amplified by an RF amplifier 151 and coupled to the RF coil 152 by a transmit/receive switch 154. The resulting signals radiated by the excited nuclei in the patient may be sensed by the same RF coil 152 and coupled through the transmit/receive switch 154 to a preamplifier 153. The amplified NMR signals are demodulated, filtered, and digitized in the receiver section of the transceiver 150. The transmit/receive switch 154 is controlled by a signal from the pulse generator module 121 to electrically connect the RF amplifier 151 to the coil 152 during the transmit mode and to connect the preamplifier 153 during the receive mode. The transmit/receive switch 154 also enables a separate RF coil (for example, a head coil or surface coil) to be used in either the transmit or receive mode.

The NMR signals picked up by the RF coil 152 are digitized by the transceiver module 150 and transferred to a memory module 160 in the system control 122. When the scan is completed and an entire array of data has been acquired in the memory module 160, an array processor 161 operates to Fourier transform the data into an array of image data. This image data is conveyed through the serial link 115 to the computer system 107 where it is stored in the disk memory 111. In response to commands received from the operator console 100, this image data may be archived on the tape drive 112, or it may be further processed by the image processor 106 and conveyed to the operator console 100 and presented on the display 104. For a more detailed description of the transceiver 150, reference is made to U.S. Pat. Nos. 4,952,877 and 4,992,736 which are incorporated herein by reference.

Referring particularly to FIG. 2, the cardiac acquisition employs a series of fast gradient echo pulse sequences, with the repetition time, TR, of each gradient echo pulse sequence of between 6 and 15 ms, depending on the type of gradient hardware available and imaging parameters chosen. These pulse sequences are executed during the interval between the cardiac trigger signals 200 referred to as the R-R interval. The length of the R-R interval is a function of the patient's heart rate.

In a fast cardiac acquisition using gradient echoes, the R-R interval is divided up into many short segments, with each segment being a fast gradient acquisition pulse sequence with a nominal flip angle of between 20°–30°. Each fast gradient echo segment acquires an NMR signal representing a single line of k-space which is sometimes referred to as a phase encoded view, or a view. Adjacent fast gradient echo segments are further combined into groups of n, where n is typically between 1 and 8. "n" is often referred to as the number of phase encoded views per segment. The data from each segment, or group, contributes to generating an image at different temporal phases of the cardiac cycle (R-R interval). The temporal location of these phase images depends on the relative time from the cardiac trigger (R-wave) 200 to the center of each group of fast gradient echo segments. In FIG. 2, the first group of 8 segments form the group 201 which acquires views for a first k-space data set 202. The next group of 8 fast gradient echo segments form another group 203 which acquires views at a second cardiac phase for a second k-space data set 204, and a third group of 8 segments form another group 205 which acquires views for a third k-space data set 206. Each group of fast gradient echo segments may employ contrast enhancement such as that disclosed in copending U.S. patent application Ser. No. 955,097, filed on Oct. 1, 1992 and entitled "Fast NMR Image Acquisition With Spectrally Selective Inversion Pulses", which is incorporated herein by reference.

The number of cardiac phases imaged during an acquisition depends on the number of groups of n phase encoded views per segment which can fit into the patient's R-R interval. Eight fast gradient echo segments are nominally chosen to constitute a group as this provides a compromise between the temporal resolution of each image (defined as the time needed to acquire data from a group of 8 segments), and the total image acquisition time. As 128 views are nominally required to form a complete image, using 8 segments per group means that 8 views of k-space are acquired per cardiac trigger. Hence, 16 cardiac triggers are needed to complete the data acquisition for a conventional MRI image, a time which is within the ability of most patients to maintain a breath-hold.

Since phase contrast MRA requires either 2 times or a minimum of 4 times the data, depending on whether it is sensitive to flow in one or three dimensions, the number of temporal cardiac phase images must be reduced if the total number of heartbeats necessary to complete the scan is kept constant. On the other hand, if the number of temporal cardiac phase images is kept constant, the number of heartbeats required to complete the scan increases by a factor of 2 or 4.

In the preferred embodiment, k-space is traversed in a sequential strip fashion during the scan. That is, phase encoded views −60 through −53 are acquired on the first cardiac trigger, phase encoded views −52 through −45 on the next cardiac trigger, and so forth. The last cardiac trigger picks up phase encoded views −64 through −61 and phase encoded views +60 through +63. This view order is preferred as it provides minimal image artifacts and also allows the central 8 low spatial frequency phase encoded views to be acquired during a single R-R interval so that image artifacts resulting from inconsistencies between cardiac triggers are minimized. Another advantage of this sequential strip view order is that phase encoded views may be shared between groups with minimal image artifacts. Significant discontinuity between k-space views are reduced in the shared data set and the central 8 phase encoded views in the shared data set are still acquired during the same R-R interval as will become apparent below.

In the preferred embodiment with 8 phase encoded views per segment, after 16 heart beats all 128 phase encoded views are acquired for each data set 202, 204 and 206. Each k-space data set 202, 204 and 206 is then employed to reconstruct an image by performing a two-dimensional Fourier transformation as is well known to those skilled in the art. The resulting images depict the heart at three successive phases of the cardiac cycle, labelled phase 1, phase 2 and phase 3 in FIG. 2. In other words, the images are an effective time average of the cardiac motion during the time interval during which their views are acquired.

The present invention increases the number of separate cardiac phase images that can be reconstructed from the acquired k-space data sets. This is accomplished by forming intermediate k-space data sets by combining selected phase encoded views from the temporally adjacent k-space data sets. As shown in FIG. 2, a first intermediate data set 208 is formed by combining four phase encoded views from the first segment 201 with four phase encoded views from the second segment 203. The temporal average of these eight combined phase encoded views is midway between cardiac phases 1 and 2, and the image reconstructed from intermediate data set 208 depicts the heart at a position midway therebetween. This is labelled phase 1.5 in FIG. 2. A similar intermediate data set 209 can be produced using eight phase encoded views from the respective second and third segments 203 and 205, and an image is reconstructed depicting the heart midway between phases 2 and 3. This is labelled phase 2.5.

Referring particularly to FIGS. 2 and 3, the intermediate data set comprises NMR data from both temporally adjacent k-space data sets. As shown in FIG. 2, this data is acquired equally from both adjacent k-space data sets and the views closest in time to the desired temporal average are selected. As shown best in FIG. 3, the first k-space data set 202 can be represented as a succession of phase encoded views ranging from phase encoded view number −64, through zero, to phase encoded view number +63. As explained above, eight of these phase encoded views are acquired as a group during each cardiac cycle, and all 128 phase encoded views are acquired, therefore, in 16 successive cardiac cycles. One such group of eight phase encoded views is shown in FIG. 3, for example, at 220 with the first four phase encoded views indicated by band 221 and the second four phase encoded views indicated by cross hatched band 222. The second k-space data set 204 is acquired in the same fashion, but at a later cardiac phase. The same k-space group of eight phase encoded views is indicated at 224, with the first four phase encoded views indicated as cross hatched band 225 and the last four phase encoded views indicated as band 226. The intermediate k-space data set 208 is formed by combining interleaved bands of phase encoded views from the temporally adjacent data set 202 and 204 as shown. The eight phase encoded view groups corresponding in k-space to the groups 220 and 224 is thus formed in the intermediate k-space data set 208 by combining the four phase encoded view band 225 from data set 204 with the four phase encoded view band 222 from data set 202. The number of phase encoded views in each interleaved band can be varied, but the interleaving of four phase encoded view bands in the preferred embodiment provides best results when eight phase encoded view segments are acquired.

In the preferred embodiment the phase encoded views are acquired in groups of eight starting at −60 and progressing through k-space to view +59. During the last cardiac cycle the bottom four phase encoded views and the top four phase encoded views are acquired. As shown in FIG. 3, the top four phase encoded views are combined in the subsequent intermediate k-space data set, whereas the bottom four phase encoded views are combined in the temporally earlier intermediate k-space data set.

The present invention is employed to improve the temporal resolution of a series of angiograms depicting the flow of blood at various phases of the cardiac cycle. Angiograms are produced by two or four complete data sets with different magnetic field gradient first moments and subtracting the measured phases or complex data in the reconstructed images. The resulting "phase map" or "complex difference" is processed to produce an angiogram in which stationary tissues are suppressed and flowing blood is enhanced. A fast spin echo pulse sequence which sensitizes the acquired NMR data with a positive gradient first moment followed by a second fast spin echo pulse sequence which sensitizes the NMR data with the negative gradient first moment is described, for example, in U.S. Pat. No. 5,281,916 entitled "NMR Angiography Using Fast Spin Echo Pulse Sequences" which is incorporated herein by reference.

There are several methods in which the view sharing concept of the present invention can be used to produce intermediate temporal phase images for phase contrast angiography. When more than one phase encoded view (labeled $P_1$ and $P_2$) is acquired per segment, an intermediate temporal phase angiogram can be produced by sharing the phase encoded views as illustrated in FIG. 6. This embodiment enables the phase contrast angiogram acquisitions to be acquired in a single breath-hold. Also note that for three-dimensional acquisitions the phase encoded views $P_1$ and $P_2$ may be encoding position along either the in-plane or the slice direction.

An alternative embodiment of the view sharing concept for phase contrast angiography is to share among the flow encoded views. This becomes necessary, for example, when only one phase encoded view per segment is acquired.

Figure 4:
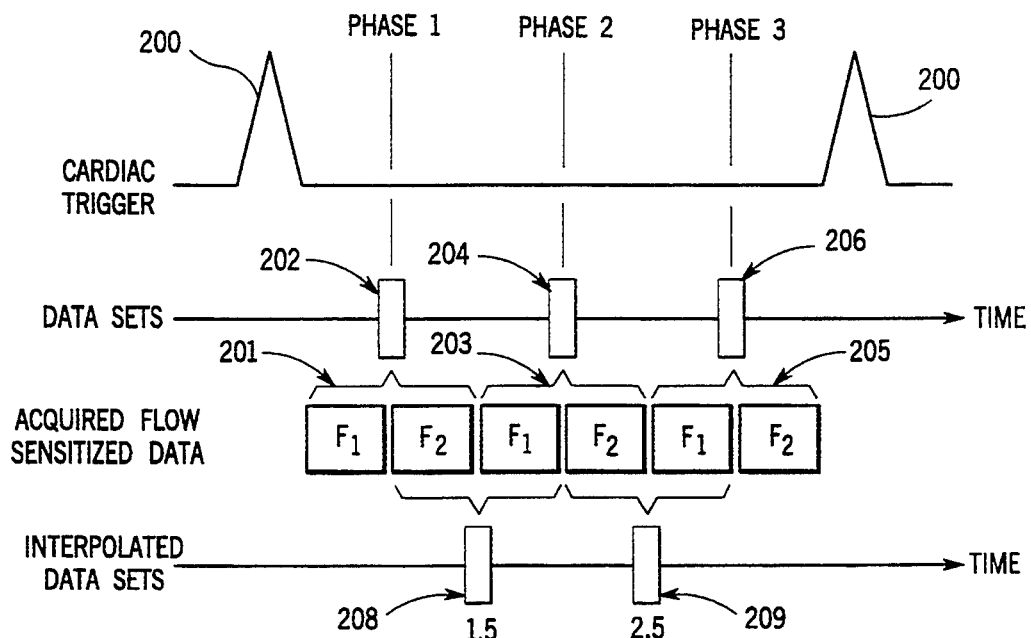
FIG. 4 is a graphic representation of a data acquisition sequence for phase contrast angiography sensitive to flow in a single direction.

Referring particularly to FIG. 4, the first data set 202 depicting the heart at phase 1 is acquired as two separate sets of flow encoded views 201 labelled $F_1$, and $F_2$. The $F_1$ flow encoded views are acquired with positive gradient first moments and the $F_2$ flow encoded views are acquired immediately thereafter with a negative gradient first moment. Similarly, the second data set 204 depicting the heart at phase 2 of the cardiac cycle is acquired as two separate sets of flow encoding views 203 and the third data set 206 is acquired as two separate sets of flow encoding views 205.

By combining the $F_1$ flow encoding views from the acquisition 201 at phase 1 with the $F_2$ flow encoding views from the acquisition 203 at phase 2, an angiogram can be produced by the combined data set 208 which depicts the vasculature midway between temporal cardiac phases 1 and 2. This has been labelled phase 1.5. Note that since the order of the flow encoded views is reversed in phase 1.5, the reconstruction process must either reverse the order by re-sorting, or by negating the calculated difference. Similarly, the $F_2$ flow encoding views from acquired data 203 at phase two is combined with the $F_1$ flow encoding views from acquired data 205 at phase three to produce data set 209. An angiogram is produced with this combined data set 209 which depicts the blood flow at cardiac phase 2.5.

The same concept may be expanded to produce angiograms from four separately flow encoded sets of views. As described by N. J. Pelc et al in "Encoding Strategies for three-Direction Phase-Contrast MR Imaging if Flow," *JMRI* 1991; 1:405–413, when the angiogram is to indicate flow in all three dimensions, at least four separate flow encoded sets of views must be acquired. For example, one reference set of flow encoded views may have zero gradient first moments and the three remaining sets of flow encoded views will have gradient first moments along the respective coordinate axes, x, y and z. Other possible flow encoding strategies are discussed in Bernstein M. A., Shimikawa A., Pelc N. J. "*Minimizing TE In Moment-Nulled Or Flow Encoded 2 and 3D Gradient Echo Imaging,*" JMRI 1992; 2:583–588. From these four sets of views images depicting flow along the three axes x, y and z can be reconstructed and combined to produce a single angiogram sensitive to flow in all three directions.

Figure 5:
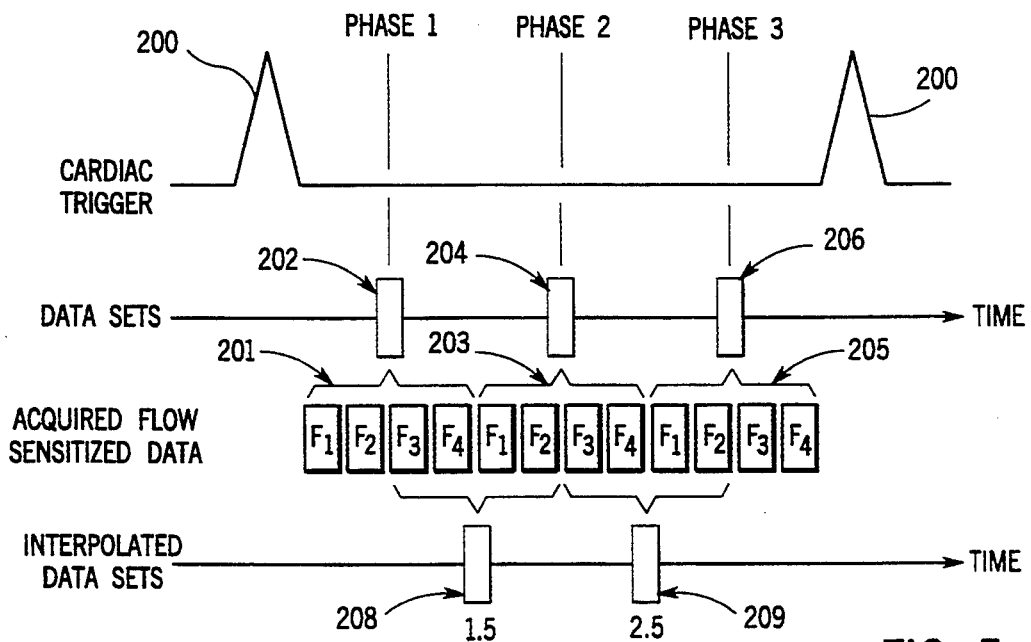
FIG. 5 is a graphic representation of a data acquisition sequence for phase contrast angiography sensitive to flow in all three dimensions

Referring particularly to FIG. 5, the present invention is employed to increase the temporal resolution of a series of angiograms sensitive to flow in all three dimensions. In this embodiment four successive sets of flow encoded views 201 labelled $F_1$–$F_4$ are acquired early in the cardiac cycle and combined to form a single data set 202 from which a three-dimensional angiogram depicting blood flow at phase 1 is reconstructed. Similarly, four separate sets ($F_1$–$F_4$) of flow encoded views 203 are acquired and used in data set 204 to reconstruct an angiogram at phase 2; and four separate sets ($F_1$–$F_4$) of flow encoded views 205 are acquired and combined in data set 206 to produce an angiogram at cardiac phase 3.

Two additional angiograms sensitive to flow in all three directions may be produced from the same data. The flow encoded views $F_3$ and $F_4$ from the acquisitions 201 are combined with the flow encoded views $F_1$ and $F_2$ from the subsequent acquisitions 203 to form the data set 208. The data set 208 contains all four sets of flow encoded views $F_1$–$F_4$ from which a three-dimensional angiogram may be produced. This angiogram depicts flow at a cardiac phase-intermediate phases 1 and 2 and is labelled 1.5. Since the order of the flow encoded views in phase 1.5 is scrambled (i.e. $F_3$ $F_4$ $F_1$ $F_2$ instead of $F_{F1}$ $F_2$ $F_3$ $F_4$), they must be re-sorted prior to image reconstruction or the differences suitably negated. The same temporal interpolation is repeated to form a second interpolated data set 209 from which an angiogram at cardiac phase 2.5 is produced. The interpolated data set 209 combines flow encoded views F3 and F4 from acquisitions 203 with flow encoded views $F_1$ and $F_2$ from acquisitions 205.

In the preferred embodiments described above a phase contrast angiogram is produced by either sharing phase encoding views when more than one phase encoding view is acquired per segment, or sharing flow encoding views when one phase encoding view per segment is acquired. As illustrated in FIG. 7, it is also possible to combine flow encoding views when more than one phase encoding view per segment is acquired. In this example two phase encoding views for an intermediate angiogram are produced.

It should be apparent to those skilled in the art that many variations are possible from the preferred embodiment without departing from the spirit of the invention. For example, the number (n) of k-space data sets acquired during each cardiac cycle can vary and the number (n−1) of intermediate k-space data sets will vary accordingly. Similarly, the number (n) of angiogram data sets acquired during each cardiac cycle can vary and the number (n−1) of intermediate angiogram data sets will vary accordingly. Other fast pulse sequences can be used to acquire each view and the view order and combining scheme can be altered. In addition, the invention may be employed with either retrospective or prospective cardiac gating, although prospective gating with continuous RF excitation is preferred.

We claim:

1. A method for increasing the number of angiographic images produced from NMR data acquired during a succession of cardiac cycles, the steps comprising:
    a) producing a cardiac signal which indicates phase of the patient's heart during each cardiac cycle;
    b) acquiring first NMR data at a first cardiac phase during each of said succession of cardiac cycles and storing said first NMR data to form a first data set;
    c) acquiring second NMR data at a second cardiac phase during each of said succession of cardiac cycles and storing said second NMR data to form a second data set;
    d) reconstructing a first angiographic image from said first data set depicting blood flow at said first cardiac phase;
    e) reconstructing a second angiographic image from said second data set depicting blood flow at said second cardiac phase;
    f) selecting NMR data from said first and second data sets to form an additional, intermediate data set; and
    g) reconstructing an additional, intermediate angiographic image from said additional, intermediate data set to depict blood flow at a cardiac phase between said first and second cardiac phases.

2. The method as recited in claim 1 in which the first NMR data includes a plurality of sets of views and each set of views is differently flow encoded, the second NMR data includes a plurality of second sets of views and each second set of views is differently flow encoded in substantially the same manner as the plurality of sets of views in the first NMR data, and in which step f) is performed by selecting one of said sets of views from the first NMR data and one of said second sets of views from the second NMR data, and wherein the views in said one of said second sets of views is flow encoded differently than the views in said one of said sets of views.

3. The method as recited in claim 2 in which the intermediate data set is formed from views in said first and second data sets which are acquired temporally adjacent to each other.

4. The method as recited in claim 1 which includes: acquiring additional NMR data at additional cardiac phases during each of said succession of cardiac cycles and storing said additional NMR data to form corresponding additional data sets and to thereby form a total of n data sets from NMR data acquired at n different cardiac phases; and step g) is performed n−1 times to reconstruct n−1 intermediate angiographic images from the n data sets.

5. The method as recited in claim 1 in which the angiographic images are reconstructed by performing a Fourier transformation on the first, second, and intermediate data sets.

6. The method as recited in claim 1 in which the first and second NMR data sets include views which are separately phase encoded and flow encoded, and the intermediate NMR data set is formed by selecting views from the first NMR data set which are phase encoded differently than the views selected from the second NMR data set.

7. The method as recited in claim 1 in which the first and second NMR data sets include views which are separately phase encoded and flow encoded, and the intermediate NMR data set is formed by selecting views from the first NMR data set which are flow encoded differently than the views selected from the second NMR data set.

8. The method as recited in claim 7 in which the views of the intermediate data set are re-ordered prior to reconstructing the intermediate angiographic image.

9. The method as recited in claim 7 in which the angiographic image is reconstructed by calculating the difference between the differently flow encoded views in the intermediate data set, and the reconstruction includes negating some of the calculated differences.

* * * * *